US007157552B2

(12) United States Patent
Ke et al.

(10) Patent No.: US 7,157,552 B2
(45) Date of Patent: Jan. 2, 2007

(54) MUTANT TRICHOSANTHIN

(75) Inventors: Yi-Bao Ke, Shanghai (CN); Hui-Ling Nie, Shanghai (CN)

(73) Assignee: Beijing STM Biotech Ltd., Beijing (CN)

( * ) Notice: Subject to any disclaimer, the term of this patent is extended or adjusted under 35 U.S.C. 154(b) by 64 days.

(21) Appl. No.: 09/905,247

(22) Filed: Jul. 13, 2001

(65) Prior Publication Data

US 2004/0197853 A1   Oct. 7, 2004

(30) Foreign Application Priority Data

| Aug. 2, 2000 | (CN) | ............................... 00 1 19553 |
| Jan. 18, 2001 | (CN) | ............................... 01 1 03102 |

(51) Int. Cl.
*A61K 38/00* (2006.01)

(52) U.S. Cl. .................................. 530/300; 514/12
(58) Field of Classification Search ............... 435/69.1; 530/300; 514/12
See application file for complete search history.

(56) References Cited

U.S. PATENT DOCUMENTS

| 5,077,390 A | 12/1991 | Wu et al. ................... 530/370 |
| 5,128,460 A | 7/1992 | Piatak, Jr. et al. |
| 5,532,214 A | 7/1996 | Lee-Huang et al. ........... 214/2 |
| 5,541,110 A * | 7/1996 | Siegall ..................... 435/252.3 |

OTHER PUBLICATIONS

Chow, T.P., et al., Isolation and DNA Sequence of a Gene Encoding Alpha-trichosanthin, a Type I Ribosome-inactivating Protein, J.Biol.Chem. 265(15): 8670-8674, 1990.
Shaw, P.C., et al., Cloning of Trichosanthin cDNA and its Expression in *Escherichia Coli*, Gene, 97(2): 267-272, 1991.
McGrath, M.S., et al., GLQ233: An Inhibitor of Human Immunodeficiency Virus Replication in Acutely and Chronically Infected Cells of Lymphocyte and Mononuclear Phagocyte Lineage, Pro. Nat'l. Acad. Sci. USA, 86:2844-2848, 1989.
Ke Y.B., et al., Structure-function Relationship of Trichosanthin, Life Sciences, 60(7):465-472, 1997.
Nie, H.L., et al., Position 120-123, A Potential Active Site of Trichosanthin, Life Sciences, 62(6):491-500, 1998.
*The Cloning and Structural Analysis Trichosanthin Gene*, Nie HL, Guo YW, et al., The 4th China Conference on Gene Structure Cloning and Expression, Haikou, A-23, 1991 (English Translation Provided).
*The Toxic Effect and Its Mechanism of Trichosanthin Against Stomach and Colon Cancer Cells*, Wu YX, Xiang DN, Zhang SP et al., Chinese Journal of Digestion, 13 (3): 263-266, 1993.
*Proteolysis of Mouse Anti-TCS IgE Monoclonal Antibody and Preparation of Its Fab*, He XH et al., Chinese Biochemistry Journal, 11(6), Dec. 1995.
*Activation of G Protein on the Membrane of TCS-Sensitive Cells*, Wu ZH, et al., Acta Biologiae Experimentalis Sinica.
*Effects of Chemical Modification of Lysine and Arginine Residues of Trichosanthin on Its Reactivity With IgE*, He XH et al., Acta Biochemica et Biophysica Sinica, 26: 657-662, 1994.
*Study on Trichosanthin Induced Apoptosis of Leukemia K562 Cells*, Kong M et al., Acta Biologiae Experimentalis Sinica, 31(3): 233-243, 1998.
Xian-Hui He et al., "Site-Directed Polyethylene Glycol Modification of Trichosanthin: Effects on its Biological Activities, Pharmacokinetics, and Antigenicity" Life Sciences, vol. 64, No. 14, Feb. 26, 1999, pp. 1163-1175.
Xian-Hui He et al., "Reducing the Immunogenicity and Improving the In Vivo Activity of Trichosanthin by Site-Directed Pegylation" Life Sciences, vol.65, No. 4, 1999, pp. 355-368.
Siu-Hong Chan et al., "Engineering of Mini-Trichosanthin That Has Lower Antigenicity by Deleting Its C-Terminal Amino Acid Residues" Biochemical and Biophysical Research Communications, vol. 270, No. 1, Apr. 2, 2000, pp. 279-285.
Yu Wang et al., "Scientific evaluation of Tian Hua Fen (THF) history, chemistry and application", Pure Appl Chem, May 1986, vol. 58, No. 5, pp. 789-798.
Sandrine Mulot et al., "The antigenic sites of trichosanthin, a ribosome-inactiviating protein with multiple pharmacological properties" Life Sciences, vol. 61, No. 23, Oct. 31, 1997, pp. 2291-2303.
Database EMBL (Online) Jul. 5, 1995, "Trichosanthes Kirilowii Trichosanthin Gene, Partiel CDS" (retrieved from EBI Accession No. EM PRO:U25676 Database Accession No. U25675).

* cited by examiner

*Primary Examiner*—Robert A. Wax
*Assistant Examiner*—Anand Desai
(74) *Attorney, Agent, or Firm*—Darby & Darby

(57) ABSTRACT

This invention relates to a mutant trichosanthin (MTCS) protein and a process for preparing the same. The product of the present invention is largely reduced of antigenicity compared to native trichosanthin (TCS), while retaining the biological activities of native TCS, e.g., anti-tumor, anti-virus, abortifacient, and ribosome-inactivating protein activities. The MTCS according to the present invention is useful as a therapeutic agent of high potency and low toxicity for the treatment of cancer, AIDS, ectopic pregnancy and for inducing mid-term abortion. Low antigenicity allows safe multiples of MTCS.

14 Claims, 1 Drawing Sheet

Fig. 1

```
                                                              ATG ATC AGA
                                                              Met Ile Arg
TTC TTA GAC CTC TCT TTG CTA ATT CTC ACC CTC TTC CTA ACA ACT CCT GCT GTG GAG GGC
Phe Leu Val Leu Ser Leu Leu Ile Leu Thr Leu Phe Leu Thr Thr Pro Ala Val Glu Gly

GAT GTT AGC TTC CGT TTA TCA GGT GCA ACA AGC AGT TCC TAT GGA GTT TTC ATT TCA AAT
Asp Val Ser Phe Arg Leu Ser Gly Ala Thr Ser Ser Ser Tyr Gly Val Phe Ile Ser Asn
 1                                    10                                      20
CTG AGA AAA GCT CTT CCA AAT GAA AGG AAA CTG TAC GAT ATC CCT CTG TTA CGT TCC AGT
Leu Arg Lys Ala Leu Pro Asn Glu Arg Lys Leu Tyr Asp Ile Pro Leu Leu Arg Ser Ser
                                      30                                      40
CTT CCA GGT TCT CAA CGC TAC GCA TTG ATC CAT CTC ACA AAT TAC GCC GAT GAA ACC ATT
Leu Pro Gly Ser Gln Arg Tyr Ala Leu Ile His Leu Thr Asn Tyr Ala Asp Glu Thr Ile
                                          50                                  60
TCA GTG GCC ATA GAC GTA ACG AAC GTC TAT ATT ATG GGA TAT CGC GCT GGC GAT ACA TCC
Ser Val Ala Ile Asp Val Thr Asn Val Tyr Ile Met Gly Tyr Arg Ala Gly Asp Thr Ser
                                      70                                      80
TAT TTT TTC AAC GAG GCT TCT GCA ACA GAA GCT GCA AAA TAT GTA TTC AAA GAC GCT ATG
Tyr Phe Phe Asn Glu Ala Ser Ala Thr Glu Ala Ala Lys Tyr Val Phe Lys Asp Ala Met
                                      90                                     100
CGA AAA GTT ACG CTT CCA TAT TCT GGC AAT TAC GAA AGG CTT CAA ACT GCT GCA GGC AAA
Arg Lys Val Thr Leu Pro Tyr Ser Gly Asn Tyr Glu Arg Leu Gln Thr Ala Ala Gly Lys
                                     110                                     120
ATA AGG GAA AAT ATT CCG CTT GGA CTC CCT GCT TTG GAC AGT GCC ATT ACC ACT TTG TTT
Ile Arg Glu Asn Ile Pro Leu Gly Leu Pro Ala Leu Asp Ser Ala Ile Thr Thr Leu Phe
                                     130                                     140
TAC TAC AAC GCC AAT TCT GCT GCG TCG GCA CTT ATT GTA CTC ATT CAG TCG ACG TCT GAG
Tyr Tyr Asn Ala Asn Ser Ala Ala Ser Ala Leu Met Val Leu Ile Gln Ser Thr Ser Glu
                                     150                                     160
GCT GCG AGG TAT AAA TTT ATT GAG CAA CAA ATT GGG AAG CGT GTT GAC AAA ACC TTC CTA
Ala Ala Arg Tyr Lys Phe Ile Glu Gln Gln Ile Gly Lys Arg Val Asp Lys Thr Phe Leu
                                     170                                     180
CCA AGT TTA GCA ATT ATA AGT TTG GAA AAT AGT TGG TCT GCT CTC TCC AAG CAA ATT CAG
Pro Ser Leu Ala Ile Ile Ser Leu Glu Asn Ser Trp Ser Ala Leu Ser Lys Gln Ile Gln
                                     190                                     200
ATA GCG AGT ACT AAT AAT GGA CAG TTT GAA AGT CCT GTT GTG CTT ATA AAT GCT CAA AAC
Ile Ala Ser Thr Asn Asn Gly Gln Phe Glu Ser Pro Val Val Leu Ile Asn Ala Gln Asn
                                     210                                     220
AA CGA GTC ACG ATA ACC AAT GTT GAT GCT GGA GTT GTA ACC TCC AAC ATC GCG TTG CTG
Gln Arg Val Thr Ile Thr Asn Val Asp Ala Gly Val Val Thr Ser Asn Ile Ala Leu Leu
                                     230                                     240
CTG AAT AGA ACA AAT ATG GCA  ↓  GCC ATG GAT GAC GAT GTT CCT ATG ACA CAG AGC TTT
Leu Asn Arg Asn Asn Met Ala     Ala Met Asp Asp Asp Val Pro Met Thr Gln Ser Phe
                           247
GGA TGT GGA AGT TAT GCT ATT TAG
Gly Cys Gly Ser Tyr Ala Leu End
```

MUTANT TRICHOSANTHIN

This application claims priority under 35 U.S.C. §119(a)–(d) to Chinese patent application serial number 00119553.0, filed on Aug. 2, 2000 and Chinese patent application serial number 001103102.6, filed on Jan. 18, 2001.

FIELD OF THE INVENTION

This invention relates to mutant trichosanthin (MTCS) proteins, a process for preparing the same, and their use.

BACKGROUND OF THE INVENTION

Trichosanthin (TCS) is originally isolated from the root tuber of a Chinese medicinal herb Trichosanthes kirilowii Maximowicz and is identified as the active component of Tian Hua Fen, a Chinese medicine described and used clinically as early as two thousand years ago. Chemically, TCS is a 27 kDa sized type I ribosome-inactivating protein (RIP). It possesses RNA-N-glycosidase activity that inactivates the 60S subunits of the eukaryotic ribosomes (Zhang J S, Liu W Y, The Mechanism of Action Trichosanthin on Eukaryotic Ribosome RNA N-glycosidase of the Cytotoxin, Nucleic Acids Res, 20 (6): 1271–1275, 1992). Native TCS is composed of 247 amino acid residues. Its primary structure is shown in FIG. 1 (Nie H L, et al., The Cloning and Structural Analysis of Trichosanthin Gene, The 4$^{th}$ China Conference on Gene Structure Cloning and Expression, Haikou, A-23, 1991). TCS has been used clinically in China since the 1970's to induce mid-term abortion and to treat diseases of trophoblastic origin, e.g., hydatiform mole (Second Research Group of Shanghai Institute of Experimental Biology, Science in China, 19: 811–830, 1976). Soon after the laboratory finding in 1989 that TCS appeared to inhibit the HIV-1 replication in both acutely infected T-lymphoblastoid cells and in chronically infected macrophages (McGrath M S, Hwang K M, Caldwell S E, et al., GLQ233: An Inhibitor of Human Immunodeficiency Virus Replication in Acutely and Chronically Infected Cells of Lymphocyte and Mononuclear Phagocyte Lineage, Proc. Natl. Acad. Sci. USA, 86: 2844–2848, 1989), clinical trials of TCS as a potential treatment for AIDS were carried out. In addition to HIV, TCS is capable of attacking other types of virus. It was also found toxic to leukemia cells and other types of tumor cells (Kong M, Ke Y B, Zhou M Y, et al., Study on Trichosanthin Induced Apoptosis of Leukemia K562 Cells, Acta Biologiae Experimentalis Sinica, 31(3): 233–243, 1998; Zheng Y T, Zhang K L, Ben K L, et al., In Vitro Immunotoxicity and Cytotoxicity of Trichosanthin Against Human Normal Immunocytes and Leukemia-lymphoma Cells, Immunopharmacology and Inimunotoxicology, 17 (1): 69–79, 1995; Wu Y X, Xiang D N, Zhang S P, et al., The Toxic Effect and Its Mechanism of Trichosanthin Against Stomach and Colon Cancer Cells, Chinese Journal of Digestion, 13 (3): 263–266, 1993). In clinical uses, however, a dangerous complication was observed with the drug. It can occasionally cause immediate type allergic reaction mediated by innimnoglobulin E (IgE) antibody. The TCS specific IgE reacts to TCS in the body, initiating the onset of type I hypersensitivity manifested clinically as complications such as allergic urticaria, angioedema, and anaphylactic shock—a sudden, severe life-threatening allergic reaction that can kill within minutes. This dysfunctional immune response to TCS usually remains strong in the recipient's body for many years. As a result, TCS is restricted to only one administration during the recipient's lifetime as an abortifacient. Not only in abortion, allergic reactions were also present when TCS was used in treating other diseases. Its application was therefore greatly restricted.

The purpose of the present invention is to remove the side effects of TCS by developing a novel TCS product with reduced antigenicity that allows safe multiple administrations.

SUMMARY OF THE INVENTION

The present invention provides a mutant trichosanthin (MTCS) protein of low antigenicity, comprising the amino acid sequence of native trichosanthin (TCS), with the modification of at least one amino acid residue in the following three regions: amino acid residues 174 to 180, 203 to 226, and 230 to 244; or a fragment or derivative of said MTCS protein containing said modification and substantially retaining the biological activities of the native TCS.

The present invention further relates to a nucleic acid encoding a MTCS according to the present invention.

The present invention further relates to a vector, esp., an expression vector containing a nucleic acid according to the present invention and a host cell transformed with a nucleic acid according to the present invention or with a vector according to the present invention.

The present invention further relates to a process for preparing a MTCS of the present invention, comprising culturing a host cell according to the present invention under a favorable condition for the expression of said MTCS, and recovering said MTCS from the culture.

The present invention further relates to a pharmaceutical composition comprising a MTCS according to the present invention and a pharmaceutically acceptable carrier or excipient.

The present invention further relates to a MTCS according to the present invention as a medicament.

The present invention further relates to a use of a MTCS according to the present invention for preparing a medicament for treating a viral disease, for treating tumor, for treating ectopic pregnancy and/or for inducing abortion.

Finally, the present invention relates to a method for inducing abortion, for treating ectopic pregnancy, for treating viral diseases and/or for treating tumors in a mammal, comprising administering to said mammal a therapeutically effective amount of a MTCS according to the present invention.

BRIEF DESCRIPTION OF THE DRAWINGS

FIG. 1 presents the amino acid sequence of the native TCS (SEQ ID NO.1 in the Sequence Listing) and the nucleotide sequence coding the same (SEQ ID NO.2). The region of positions 1 through 247 shows the amino acid sequence of the mature native TCS. The mature native TCS (amino acids 1 through 247) are also set forth as SEQ ID NO:8.

DETAILED DESCRIPTION OF THE PREFERRED EMBODIMENT

The present inventors have discovered after extensive studies that the immunological reactive regions of TCS are structurally located at amino acid residues between 174 to 180, 203 to 226, and 230 to 244. The modification of at least one amino acid residue within these three regions can produce a novel MTCS protein with excellent properties. The antigenicity of TCS is largely reduced in the MTCS while the biological activities of TCS being substantially retained in the MTCS. A MTCS according to the present invention retains at least RIP activity and abortifacient activity, and preferably retains all of the biological activities including anti-tumor and anti-virus activities.

Thus, the present invention provides a MTCS of low antigenicity, wherein at least one amino acid residue is modified in the following three regions of the amino acid sequence of TCS: amino acid residues 174 to 180, 203 to 226, and 230 to 244.

The numerical positions of amino acid residues mentioned in the description and claims of this application refer to the residue numbers as shown in FIG. 1 and SEQ ID NO:8.

The MTCS according to the present invention can be a full-length mature protein or a fragment or a derivative thereof containing at least one modification of amino acid residue as defined in the present invention.

As used in this application, the term "modification" of amino acid residue refers to the deletion, insertion, addition, replacement, or chemical modification. In a preferred embodiment, the modification of amino acid residue causes a change in the electric charge of the amino acid site where the same modification is being made. The term "replacement" of amino acid residue preferably refers to replacing a hydrophilic amino acid residue with a hydrophobic amino acid residue, replacing a hydrophobic amino acid residue with a hydrophilic amino acid residue, replacing an acidic amino acid residue with a basic amino acid residue, or replacing a basic amino acid residue with an acidic amino acid residue.

The term "hydrophilic amino acid" used here particularly refers to serine (Ser), threonine (Thr), cysteine (Cys), tyrosine (Tyr), aspartic acid (Asp), asparagine (Asn), glutamic acid (Glu), glutamine (Gln), lysine (Lys), arginine (Arg), and histidine (His). Among these hydrophilic amino acids, Asp, Asn, Glu, and Gln are acidic amino acids, and Lys, Arg and His are basic amino acids. The term "hydrophobic amino acid" particularly refers to glycine (Gly), alanine (Ala), valine (Val), leucine (Leu), isoleucine (Ile), proline (Pro), phenylalanine (Phe), tryptophan (Try), and methionine (Met).

In a preferred embodiment of the invention, the region 174–180 of the MTCS contains at least one amino acid residue modification selected from Table 1.

TABLE 1

| Original Amino Acid Residue & its Numerical Position | Preferred Modification |
|---|---|
| Arg174 | Replaced by Glu, Asp, or Gly |
| Val175 | Deleted |
| Asp176 | Replaced by Lys or Gly |
| Lys177 | Replaced by Glu, Asp, or Gly |
| Thr178 | Replaced by Gly, or Ala |
| Phe179 | Deleted |
| Leu180 | Deleted |

In another preferred embodiment of the invention, the region 203–226 of MTCS contains at least one amino acid residue modification selected from Table 2.

TABLE 2

| Original Amino Acid Residue & its Numerical Position | Preferred Modification |
|---|---|
| Ser203, Ser 211 | Replaced by Gly or Ala |
| Thr204, Thr224, Thr226 | Replaced by Gly or Ala |
| Asn205, Asn206, Asn217, Asn220 | Replaced by Lys or Gly |
| Gly207 | Deleted |
| Gln208, Gln219, Gln221 | Replaced by Lys or Gly |
| Phe209 | Deleted |
| Glu210 | Replaced by Lys or Gly |
| Pro212 | Deleted |
| Val213, Val214, Val215, Val223 | Deleted |
| Ile216, Ile225 | Deleted |
| Ala218 | Deleted |
| Arg222 | Replaced by Glu, Asp or Gly |

In another preferred embodiment of the invention, the region 230–244 of MTCS contains at least one amino acid residue modification selected from Table 3.

TABLE 3

| Original Amino Acid Residue & its Numerical Position | Preferred Modification |
|---|---|
| Ala230, Ala238 | Deleted |
| Gly231 | Deleted |
| Val232, Val233 | Deleted |
| Thr234 | Replaced by Gly or Ala |
| Ser235 | Replaced by Gly or Ala |
| Asn236, Asn242, Asn 244 | Replaced by Lys or Gly |
| Ile 237 | Deleted |
| Leu239, Leu240, Leu241 | Deleted |
| Arg243 | Replaced by Glu, Asp or Gly |

Preferably, the MTCS of the present invention contains amino acid residue modifications in two or three of said three regions of 174–180, 203–226 and 230–244. Even more preferably in this embodiment, modifications in each of these regions are selected from Table 1, Table 2 and Table 3 respectively.

In a preferred embodiment, the MTCS of the present invention contains both of the following amino acid residue modifications: replacing Lys at position 177 with Glu, and replacing Ser at position 203 with Gly.

In a still preferred embodiment, the MTCS of the present invention contains all of the following three amino acid residue modifications: replacing Lys at position 177 with Glu, replacing Ser at position 203 with Gly, and replacing Asn at position 236 with Gly.

The present invention further relates to a nucleic acid encoding a MTCS of the present invention.

The MTCS of the present invention can be prepared by methods of genetic engineering or peptide synthesis, e.g., solid-phase peptide synthesis (Merrifield J, J Am Chem Soc 85:2149–2154, 1963), both of which are well known to those skilled in the art. Preferably, MTCS is prepared by modifying native TCS gene and then expressing said modified gene in an appropriate biological host.

The nucleic acid of the present invention encoding said MTCS can be cloned into an appropriate vector, esp., an expression vector, e.g., plasmid vectors pET-2d or pET-3a.

The nucleic acid of the present invention or a vector containing said nucleic acid can be used to transform an appropriate host cell, e.g., Escherichia Coli (E. Coli.). A resultant transformed host cell can be cultured to produce the MTCS of the present invention. The present application also relates to such transformed host cells.

Therefore, the present invention further relates to a process for preparing a MTCS according to the present invention, comprising culturing a host cell of the present invention under a favorable condition for the expression of said MTCS, and recovering said MTCS from the culture.

Native TCS gene is composed of 870 base pairs from ATG (the initiation codon) to TAG (the termination codon). For those skilled in the art, said gene can be obtained, based on the published information on its sequence, following standard methods, e.g., by isolation from a genomic DNA library (Chow T P, Feldman R A, Lovett M, Piatak M, et al., Isolation and DNA Sequence of a Gene Encoding Alpha-trichosanthin, a Type I Ribosome-inactivating Protein, J. Biol. Chem. 265(15): 8670–8674, 1990) or a cDNA library (Shaw P C, Yung M H, Zhu R H, Ho W K, Ng T B, Yeung H W, et al., Cloning of Trichosanthin cDNA and its Expression in *Escherichia Coli*, Gene, 97 (2): 267–72, 1991), by using the polymerase chain reaction (PCR) (Nie H L, et al., The Cloning and Structural Analysis of Trichosarithin Gene, The 4$^{th}$ China Conference on Gene Structure Cloning and Expression, Haikou, A-23, 1991), or by chemical synthesis. Said gene encodes a prepro-protein composed of 289 amino acids. In addition to the mature native TCS of 247 amino acid residues, the prepro-protein contains a 23 mer signal peptide at the N-terminus and a 19 mer tail peptide at the C-terminus. The cDNA encoding TCS prepro-protein can be conveniently cloned using a previously published method (Sambrook J, et al., Molecular Cloning, A laboratory Manual (Second Edition), Cold Spring Harbor Laboratory Press, 1982). A plasmid comprising said cDNA can also be used directly.

Native TCS gene can be modified using site-directed mutagenesis, a technique well known to those skilled in the art. In one embodiment of the invention, said modification comprises a) Creating, when necessary, appropriate restriction enzyme sites before the 5' terminus and after the 3' terminus of the DNA sequence encoding mature native TCS and introducing an initiation codon and a termination codon respectively. For example, a restriction enzyme NcoI site (CCATGG) before the 5' terminus of the DNA sequence encoding mature native TCS can be created to introduce an initiation codon ATG, and to add a Met at the −1 position of the mature native TCS, or a restriction enzyme NdeI site (CATATG) can be created to replace the amino acid residue at the 1 position of the mature native TCS from Asp to Met. After the 3' terminus of the DNA sequence encoding mature native TCS, a restriction enzyme BamHI site (GGATCC) can be created to introduce a termination codon; and b) Modifying the DNA sequences encoding the amino acid sequences to be mutated (amino acid residues in the regions of 174–180, 203–226, and 230–244) to obtain the gene of the MTCS of the present invention. Due to codon degeneracy, multiple schemes of genetic mutation can be used in order to modify one amino acid residue. Commercially available kits, e.g., Muta-Gene Phagemid in vitro Mutagenesis Kit from Bio-Rad Co., are well designed for carrying out mutations of specific DNA sites. Protocols can be followed according to manufacturer's instructions.

The DNA sequence encoding MTCS obtained from site-directed mutagenesis can be digested by appropriate restriction enzyme, e.g., NcoI (or NdeI) and BamHI, and then cloned into an expression vector e.g., plasmid vector pET-2d (or pET-3a). The resultant mutant expression vector can be used to transform an appropriate host cell, e.g., *E. Coli* BL21 (DE3, pLysS) following standard procedures. The transformant is then cultured in appropriate medium. Inducer, e.g., isopropyl-beta-D-thio-galactoside (IPTG) can be added to the culture at a proper time, if necessary, to induce expression of MTCS, which can then be collected from the culture with standard methods including lysing the host cells, centrifuging the lysate, and purification by column chromatography.

Experiments on the Activities of MTCS

Assays to determine the immunological reactivities and the biological activities of MTCS of the present invention are listed below along with the results.

1. Properties of TCS Deleting Mutants and TCS Modifying Mutants

TCS molecule is genetically modified according to the mutations listed in Tables 1 to 3 for the analysis of the relationship between its primary structure and its biological and immunological activities. Genes are obtained that encode TCS with either deletion of C terminal sequence (the deleting mutants) or modification of multiple amino acid residues (the modifying mutants). The mutant proteins are obtained correspondingly that are either deleting mutants or modifying mutants by expressing in *E. Coli* and then purifying the same. TCS and its mutants possess RNA N-glycosidase activity that inactivates ribosome and blocks cellular protein synthesis. Assays for the biological activities and the immunological reactivities are carried out for these deleting mutants and modifying mutants. The structural basis for the active regions of TCS can be analyzed according to the results of these assays along with the available information from the three dimensional structure of TCS. RIP activity is determined as described by Pelhem & Jackson (H. K. B. Pelhem and R. J. Jackson, Eur. J. Biochem. 67: 247–256, 1976). Abortifacient activity assay was conducted following standard protocols of the present inventors' laboratory (Nie H L, et al., Position 120–123, a Potential Active Site of Trichosanthin, Life Sciences, 62 (6): 491–500, 1998) In vitro immunological reactivity is measured by competitive ELISA (enzyme linked immunosorbent assay) (He X H, et al., Effects of Chemical Modification of Lysine and Arginine Residues of Trichosanthin on its Reactivity with IgE, Acta Biochemica et Biophysica Sinica, 26: 657–662, 1994). Results are listed in Table 4.

TABLE 4

Property assay of TCS deleting mutants and TCS modifying mutants.

| PRODUCT | Position of Amino Acid Deletion | Position of Amino Acid Modification | RIP Activity* | Abortifacient Activity** | In vitro Reactivity with IgG*** | In vitro Reactivity with IgE*** |
|---|---|---|---|---|---|---|
| NTCS(1-247) | N/A | N/A | ++ | ++ | ++ | ++ |
| L3TCS(1-244) | 247-245 | N/A | ++ | ++ | ++ | ++ |
| L5TCS(1-242) | 247-243 | N/A | ++ | ++ | + | + |
| L10TCS(1-237) | 247-238 | N/A | ++ | ++ | + | + |
| L14TCS(1-233) | 247-234 | N/A | ++ | ++ | + | + |
| L29TCS(1-218) | 247-219 | N/A | + | + | − | − |
| L46TCS(1-201) | 247-202 | N/A | + | + | − | − |
| L52TCS(1-195) | 247-196 | N/A | ± | ± | − | − |
| L67TCS(1-180) | 247-181 | N/A | − | − | − | − |
| L74TCS(1-173) | 247-174 | N/A | − | − | − | − |
| L7TCS (1-173, 181-247) | 180-174 | N/A | ± | ± | ± | ± |
| L52TCS (1-173, 181-202) | 247-203, 180-174 | N/A | − | − | − | − |
| M7TCS(1-247) | N/A | one of 180-174 | ++ | ++ | ± | ± |
| M24TCS(1-247) | N/A | one of 226-203 | ++ | ++ | ± | ± |
| M15TCS(1-247) | N/A | one of 244-230 | ++ | ++ | + | + |
| M31TCS(1-247) | N/A | one of 226-203, and one of 180-174 | ++ | ++ | −(a) | −(a) |
| M46TCS(1-247) | N/A | one of 244-230, and one of 226-203, and one of 180-174 | ++ | ++ | −(b) | −(b) |

NTCS - Native TCS
LTCS - TCS deleting mutant
MTCS - TCS modifying mutant
*RIP activity $IC_{50}$ (ng/ml): ++ ≦50, 50< + ≦500, 500< ± ≦5000, −>5000
**Abortifacient activity (%): ++ ≧80, 80> + ≧30, 30> ± ≧5, −<5
***In vitro immunological reactivity (%): ++ >80, 80≧ + >30, 30≧ ± >10, 10≧−(a)>5, −(b)≦5

Results of the above assays of the properties of TCS deleting mutants and TCS modifying mutants indicate the following.

For a TCS deleting mutant, when 3 amino acid residues are deleted from the C terminus, its in vitro reactivity with inimunoglobulin G (IgG) and IgE remains as strong positive as native TCS. Its immunological reactivity is reduced when the deletion is increased to 5 amino acid residues, while in this case no effect on its RIP activity or abortifacient activity is observed. Not until 29 amino acid residues are deleted is there a decrease in its biological activities. It was reported by the present inventors that the biological active center of TCS is located at positions between 110–174 (Ke Y B, Chen J K, Nie H L, et al., Structure-function Relationship of Trichosanthin, Life Sciences, 60 (7): 465–472, 1997). The three-dimensional structural change caused by deletion of C-terminal sequence also affects this active center. The closer the deleted sequence to the active center, the more the reduction of biological activities. It is now discovered that the immunological reactive region is structurally located closer to the C-terminus than the biological active center. Consequently it is more easily affected by deletion of C-terminal sequence. The modifying mutants M7TCS(1–247)[one of the amino acid residues between positions 174 to 180 is mutated], M24TCS(1–247) [one of the amino acid residues between positions 203 to 226 is mutated] and M15TCS(1–247) [one of the amino acid residues between positions 230 to 244 is mutated] in Table 4 demonstrate weak in vitro reactivities with IgG and IgB, and potent biologic activities including RIP and abortifacient activities. This result indicates that the three modified regions of amino acid sequence (positions 180–174, 226–203, 244–230) are relevant with the immunological reactivities. Any structural changes in these regions may cause the reduction of the immunological reactivities. These structural changes include the deletion of at least one amino acid residue; the insertion of at least one amino acid residue between two adjacent amino acid residues; the addition of at least one amino acid residue to these sequences; the replacement of at least one hydrophilic amino acid residue with a hydrophobic amino acid residue; the replacement of at least one hydrophobic amino acid residue with a hydrophilic amino acid residue; the replacement of at least one acidic amino acid residue with a basic amino acid residue; the replacement of at least one basic amino acid residue with an acidic amino acid residue; the coupling of at least one amino acid residue to a chemical entity; and/or any modification including insertion of at least one amino acid residue that can cause a change in the electric charge of the amino acid site where the same modification is being made. The modifying mutants M31TCS(1–247) [one of the amino acid residues between positions 174 to 180 and one of the amino acid residues between positions 203 to 226 are mutated] and M46TCS(1–247) [one of the amino acid residues between positions 174 to 180, one of the amino acid residues between positions 203 to 226 and one of the amino acid residues between positions 230 to 244 are mutated] demonstrate negative immunological reactivitie and potent biological activities including RIP and abortifacient activities. These two are the mutants of excellent properties. The antigenicity of native TCS is largely reduced. But the biological activities of native TCS are retained. The antigenicity of M46TCS(1–247) is even lower compared to M31TCS(1–247).

2. Properties of MTCS of the Present Invention

In vitro RIP activity assay, assay for abortifacient activity in mid-term pregnant mice, assay for in vitro reactivities with IgG and IgE were carried out following protocols mentioned earlier on MTCS(M177, 203) (Lys177 is replaced with Glu and Ser203 is replaced with Gly) of the present invention. Assay for toxicity to tumor cells in culture was carried out following standard protocols of the present inventors' lab (Kong M, et al., Study on Trichosanthin Induced Apoptosis of Leukemia K562 Cells, Acta Biologiae Experimentalis Sinica, 31 (3): 233–243, 1998).

a) Comparison of the immunological reactivities and the biological activities between MTCS and native TCS is listed in Table 5.

TABLE 5

Comparison of the immunological reactivities and biological activities between MTCS and native TCS

| | Native TCS | MTCS |
|---|---|---|
| RIP Activity (%) | ++ | ++ |
| Abortifacient Activity (%) | ++ | ++ |
| Toxicity to Tumor Cell (K562 Cell Line) | ++ | ++ |
| In Vitro Reactivity with IgE (%) | ++ | —[(a)] |
| In Vitro Reactivity with IgG (%) | ++ | —[(a)] |
| Induction of In Vivo IgE Response in Rats* | ++ | — |
| Induction of In Vivo Immediate Hypersensitivity in Guinea Pigs** | ++ | ± |

*See details in (c-iv)
**See details in (c-iii)

b) Toxicity of MTCS against different cell lines is listed in Table 6.

TABLE 6

Toxicity of MTCS against different cell lines

| Cell Line | $LC_{50}$ (ug/ml) |
|---|---|
| Jar | 7.0 |
| HL60 | 8.1 |
| MLT | 10.0 |
| K562 | 11.0 |
| U937 | 17.0 |
| B16 | 69.2 |
| A431 | 77.6 |
| B7-325 | 218.8 |
| SPCA1 | 257.0 |
| 7404 | 354.8 |
| Wish | >1000 |
| HPPLC* | >1000 |

*Normal human peripheral lymphocyte, collected clinically.

The median lethal concentration ($LC_{50}$) of MTCS is lower than 30 ug/ml for leukemia cell lines K562, HL60, MLT, U937 and for choriocarcinoma cell line Jar. These cell lines with $LC_{50} \leqq 30$ug/ml are regarded as the Most Sensitive Cell Lines. $LC_{50}$ of MTCS is higher than 30 ug/ml for tumor cell lines B16, A431, B7-325, SPCA1 and 7404, etc. which are designated as the Medium Sensitive Cell Lines. $LC_{50}$ of MTCS is higher than 1000 ug/ml for normal body cell lines, e.g., HMPLC and Wish (cell of the amniotic membrane), which are regarded as Non-Sensitive Cell Lines. The data clearly indicate that within a certain range of concentration, MTCS is potently toxic to leukemia cells and other types of tumor cells, while leaving normal cells intact. This result consists with previous similar studies on TCS.

c) Animal model studies c-i) Anti-tumor activity

Eight week old nude mice are subcutaneously inoculated with $1\times10^7$ cells of the human chronic myelogenous leukemia cell line K562. Inoculated cells grow in vivo and form a visible solid tumor in 50% of the animals 10 days after inoculation. Animals bearing xenograft implanted tumors are randomly divided into four groups. Animals in three groups are treated with different dosages of MTCS injection. The other group is given physiological saline as control. The MTCS dosages given for treatment are lower than or equal to the effective abortifacient dosage, being 15 nm/Kg, 45 nm/Kg, and 75 nm/Kg respectively in three groups. MTCS is administered once every four days for a total of four times. Different degrees of tumor inhibition are observed at inhibition ratio of (40±3)%, (71±2)%, and (92±4)% respectively in three treatment groups. SCID (severe combined immunodeficient) mice lacking both T and B lymphocytes are also chosen for studying the toxicity of MTCS against K562 cells. Nine-week-old SCID mice are subcutaneously inoculated with $1\times10^7$ K562 cells. 100% of the inoculated animals grow a solid tumor. Animals are randomly divided into four groups five days after the inoculation. Three of them are treatment groups. The other is physiological saline control. Animals in different treatment groups are treated with MTCS at three different dosages of high, medium, and low respectively. High dosage group—one injection of 150 nm/Kg; Medium dosage group—two injections of 75 nm/Kg each, one administration every week; Low dosage group—three injections of 37 nm/Kg each, one administration every four days. The total dosage administered is 150 nm/Kg in all groups. Tumor inhibition ratio is observed at (43±6)%, (64±8)%, and (94±3)% respectively in high, medium, and low groups. The conclusion of the results from both animal models is that MTCS has clear tumor inhibitory effects at the effective abortifacient dosage. Tumor inhibition ratio of above 90% can be achieved by four injections of a half of the effective abortifacient dosage. Multiple injections of small dosage lead to excellent results.

MTCS demonstrates excellent tumor inhibitory effects in both of the above-mentioned studies in xenograft animal models of human chronic myelogenous leukemia. Based on these animal models, another xenograft SCID—human chronic myelogenous leukemia model is established. Liquid tumor forms in the murine host after inoculation with K562 cells, and is manifested by the white blood cell count and other blood biochemistry changes of the murine host. Xenograft mice are treated with MTCS by intravenous injection at dosages of 3.75 nm/Kg, 7.5 nm/Kg, and 15 nm/Kg respectively in three treatment groups. After three injections, the percentage of mice whose white blood cell count returned to normal range is (25±6)%, (75±8)%, and (94±3)% respectively in three treatment groups. The data indicate that a smaller dosage of MTCS can be used in treating liquid tumors than in treating solid tumors. And a better result can still be achieved with liquid tumors than with solid tumors.

c-ii) Acute toxicity test in mice Acute toxicity test in mice is conducted following standard protocols. Eight-week-old F1 mice (ICR/Balb-c) are used. Each animal is given one injection of either native TCS or MTCS. Animals are observed for seven days for the comparison of median lethal dosage ($LD_{50}$) between native TCS and MTCS. Under the same dosage, a higher mortality rate and earlier death is observed with animals injected with native TCS compared to animals in MTCS group. $LD_{50}$ (native TCS)=18.4 mg/Kg, $LD_{50}$ (MTCS)=27.5 mg/Kg. The acute toxicity of MTCS is almost 50% lower than that of native TCS.

c-iii) Immediate hypersensitivity test in guinea pigs

Native TCS and MTCS are separately tested for immediate hypersensitivity in guinea pigs. Guinea pigs are sensitized by an intradermal injection of a dose 4.5 times the human abortifacient dose. Animals are challenged after fourteen days by an intravenous injection of a dose 10 times the human abortifacient dose. Animals are observed for 30 minutes upon challenge with allergen for anaphylactic reaction and death. The dead/total animal ratio in native TCS group is 12/14, about 86%. In MTCS group the ratio is 3/15, about 20%. A significant difference exits. MTCS causes a much reduced immediate allergic reaction in guinea pigs compared to native TCS.

c-iv) Passive cutaneous anaphylaxis (PCA) in rats

PCA in rats is conducted as described by Ovary (Ovary Z, et al., PCA Reactions with Mouse Antibodies in Mice and Rats, Inter Archs Allergy Appl Immun, 48: 16–21, 1975). Two groups of mice are sensitized by native TCS and MTCS separately. Mouse antiserum generated against native TCS and MTCS are obtained after fourteen days. Two group of rats are anesthetized and injected intradermally in the shaven back with native TCS and MTCS antiserum respectively, and challenged intravenously with native TCS or MTCS solution correspondingly containing 1% Evans blue dye. After 30 minutes, the animals are sacrificed and the PCA response is determined by measuring the diameter of the dorsal blue skin lesions. Skin lesion bigger than 0.5 cm is regarded as positive reaction. All animals in native TCS group show positive reactions. All animals in MTCS group are negative. The in vivo IgE response in rats induced by native TCS is drastically reduced in the case of MTCS.

3. Anti-tumor mechanism of MTCS a) MTCS Induces Apoptosis in Sensitive Cells.

As mentioned earlier in 2a and 2b, MTCS is highly toxic to leukemia cells in culture while leaving normal body cells intact. Taking the action of MTCS to K562 cells as an example, multiple studies are carried out for its mechanism. Characteristic changes in cell morphology of programmed cell death, or apoptosis, can be observed with K562 cells treated with MTCS through an electronic microscope: shrinkage of the cell body, condensation of the cytoplasm, dilation of the endoplasmic reticulum, loss of the nucleoli, margination of nuclear chromatin into discrete masses, and break-up of cells into several membrane bound bodies (i.e., apoptotic bodies). The MTCS treated cells also exhibit the oligonucleosomal DNA ladder, which is the biochemical hallmark of apoptosis, and the subdiploid apoptotic peak in fluorescence activated cell sorting (FACS) analysis. The results indicate that MTCS triggers apoptosis in K562 cells.

b) Specific binding sites of MTCS exist on the membrane of sensitive cells

Real-time Biomolecular Interaction Analysis (BIA) is used for this study. MTCS is immobilized in a dextran matrix on the sensor chip, which forms one wall of a micro-flow cell. Cell membrane extract is then injected over the surface in a controlled flow. Any change in surface concentration resulting from interaction is detected as a surface plasmon resonance (SPR) signal, expressed in resonance units (RU) Different types of sensitive cells give responses of 100–300 RU's showing strong binding of MTCS to cellular membrane protein. There are no significant binding events when a normal body cell, e.g., cell of the amniotic membrane, is used in interaction analysis.

c) It is Observed with a scanning laser confocal microscope that MTCS can be internalized into K562 cells via receptor-mediated endocytosis.

d) In GTP gamma $^{35}S$ binding assay, MTCS activates G-protein-mediated signal transduction in sensitive cells. same phenomenon cannot be observed in non-sensitive cells.

e) It is observed with a scanning laser confocal microscope that MTCS induces intracellular calcium release from the intracellular calcium store in sensitive cells.

The conclusion of anti-tumor mechanism studies is the following. Membrane receptors present in sensitive cells mediate the endocytosis of MTCS, which then exerts its RIP effect. Meanwhile, MTCS also interferes with cellular signal transduction. These two effects in combination lead to apoptosis in sensitive cells. As the great majority of sensitive cells are tumor cells, MTCS has a unique mechanism of action against tumor compared with cytotoxic or cytostatic chemotherapeutic drugs that inhibit tumor and damage normal body tissues at the same time. It provides the theoretic basis for the clinical application of MTCS as a new anti-tumor agent.

As mentioned earlier, the MTCS of the present invention is largely reduced of antigenicity compared to native TCS, while substantially retaining the biological activities of native TCS. Low antigenicity allows safer multiple administrations and better treatment of all the medical indications that can be treated by native TCS. To be more specific, the indications include but are not limited to the following items.

1. Leukemia and other types of solid tumors. Because of its selective entry mechanism into target cells, only a few administrations of small doses of MTCS are required in clinical practice. MTCS is highly toxic to tumor cells while leaving normal body cells intact within a certain range of dosage, making it very low in adverse effects.

2. Viral diseases and especially AIDS. MTCS is lower in side effects and safer to patients comparing to native TCS in treating AIDS.

3. Ectopic pregnancy and for the induction of mid-term abortion. Unlike TCS, which is restricted to only one administration during the recipient's lifetime as an abortifacient, safe multiple injections of MTCS is possible due to its low antigenicity.

The MTCS of the present invention can be included in a pharmaceutical composition together with a pharmaceutically acceptable carrier or excipient. Accordingly the invention also provides a pharmaceutical composition comprising a therapeutically effective amount of MTCS of the present invention, in combination with a pharmaceutically acceptable carrier or excipient examples of such carrier or excipient include but are not limited to one or a combination of saline, aqueous buffer solutions, dextrose solution, water, glycerin and ethanol, etc. Such pharmaceutical composition should be adapted to the chosen route of administration.

The present invention also provides a pharmaceutical package or kit comprising one or more containers filled with one or more of the ingredients of the pharmaceutical composition of the present invention. The MTCS according to the present invention and its fragments or derivatives can also be used in combination with additional therapeutic compounds.

The pharmaceutical composition according to the present invention can be administered to a mammalian host, such as a human patient in a variety of routes, e.g., oral, topical, intravenous, intraperitoneal, intramuscular, intratumor, subcutaneous, intranasal or intradermal routes. Effective amount of such pharmaceutical composition is required for use in treatment or prevention of a particular disorder or condition according to the nature of the disorder or condition. The useful dosages of MTCS of the present invention can be determined by referring to the effective dosages of native TCS.

The following examples are illustrative but are not meant to be limiting of the present invention.

EXAMPLES

Example 1

This example is illustrative of the site-directed mutagenesis of TCS gene and the cloning of the cDNA of mature native TCS.

For those skilled in the art, native TCS gene can be easily obtained following standard methods, e.g., by isolation from a cDNA library of Trichosanthes kirilowii Maximowicz using native TCS protein as the probe (Shaw P C, Yung M H, Zhu R H, Ho W K, Ng T B, Yeung H W, et al., Cloning of Trichosanthin cDNA and its Expression in *Escherichia Coli*, Gene, 97(2): 267–72, 1991), by isolation from a genomic DNA library of Trichosanthes kirilowii Maximowicz using a properly designed DNA probe (Chow T P, Feldman R A, Lovett M, Piatak M, et al., Isolation and DNA Sequence of a Gene Encoding Alpha-trichosanthin, a Type I Ribosome-inactivating Protein, J. Biol. Chem. 265(15): 8670–8674, 1990), or by polymerase chain reaction (PCR) using properly designed DNA primers (Nie H L, et al., The Cloning and Structural Analysis of Trichosanthin Gene, The 4th China Conference on Gene Structure Cloning and Expression, Haikou, A-23, 1991).

The cDNA (sequence shown in FIG. 1) of the TCS prepro-protein containing the signal peptide and the tail peptide was site-directedly mutated with mutagenic primers I and II, in a way that an initiation codon was created before the 5' terminus and a termination codon was created after the 3' terminus of the DNA sequence encoding mature native TCS. The DNA encoding mature native TCS was then cloned into an expression vector. Two mutagenic primers were designed for the experiment.

170-3576) from Bio-Rad Co. Protocols were followed according to manufacturer's instructions. The mutations were confirmed by sequencing analysis. Please refer to the manufacturer's instructions for details.

In short, this method comprises the following steps.

Extraction of Uracil-containing Template DNA

The native gene encoding TCS prepro-protein was cloned into phagemid vector pTZ-19U, thereby obtaining pTZ-19U-TCS' as the template DNA. (Nie H L, et al., The Cloning and Structural Analysis of Trichosanthin Gene, The 4.sup.th China Conference on Gene Structure Cloning and Expression, Haikou, A-23, 1991). *E. coli.* CJ236 growing in chloramphenicol-containing medium was transformed with pTZ-19U-TCS' and then spread on ampicillin-containing plates for picking individual colonies. The phagemid-carrying bacterial cells were cultured in 50 ml of ampicillin-containing medium to $O.D_{600}$ of about 0.3. Next, $1 \times 10^1$ pfu of helper phage M13K07 was added to the culture which was then incubated for 1 hour at 37° C. with aeration, and then added 3.5mg of kanamycin. After another incubation for 4 to 6 hours, the culture was centrifuged and the supernatant was mixed with 10 ug of RNase and incubated again for 30 minutes. The thus incubated mixture was precipitated with ammonium acetate/PEG for 30 minutes on ice, and centrifuged. The precipitant was resuspended in 200 ul of high-salt buffer, held on ice for 30 minutes, and centrifuged again. The uracil-containing template DNA in the supernatant was then extracted with phenol, phenol/chloroform, and chloroform. Finally, the same uracil-containing template DNA was precipitated with ammonium acetate/ethanol at −70° C., washed with 70% ethanol and resuspended in 10–20 ul of TE buffer.

Synthesis of Mutagenic Strand

The uracil-containing template DNA as obtained above was mixed with 0.1 to 0.3 pmol of mutagenic primers, annealing buffer and water. The mixture was heated to 70° C. and then allowed to cool to 30° C. over a 40-minute period. The thus cooled mixture was placed in ice-water bath and added 3 units of T4 DNA ligase and 1 unit of T4 DNA polymerase. The synthesis mixture was incubated on ice for 5 minutes, then at 25° C. for 5 minutes, and finally at 37° C. for 90 minutes. The synthesis reaction was terminated by adding 90 ul of stop buffer. Thus mutated DNA was used to transform calcium chloride-treated competent *E. coli.* MV1190. The transformant was incubated over night at 37° C. on ampicillin plates. A few individual colonies were then picked from the plates. Plasmid DNA was extracted from each of these colonies. Finally the mutations were confirmed

```
Primer I.   5' GTG CAG GCC ATG GAT GTT AGG 3'            (SEQ ID NO. 3)

Primer II.  5' AAC AAT ATG GCA TAG GAT CCC ATG GAT GAC 3'  (SEQ ID NO. 4)
```

Primer I is characterized in that it contains a restriction enzyme NcoI site (CCATGG) so as to introduce an initiation codon (ATG), and to add a methionine at the −1 position of the mature native TCS.

Primer II is characterized in that it contains a restriction enzyme BamHI site (GGATCC) so as to add a termination codon (TAG) after the 3' terminus of the DNA sequence encoding mature native TCS.

Mutagenesis was performed using the Muta-Gene Phagemid in vitro Mutagenesis Kit (Catalogue Number by sequencing analysis. In this example said plasmid DNA being pTZ-19U-TCS which contained the DNA sequence encoding mature native TCS with an NcoI site at the 5' terminus and a BamHI site at the 3' terminus.

Plasmid pTZ-19U-TCS thus obtained by mutation with primer I and primer II was further used as the template DNA in examples 2 through 6. On the other hand, plasmid pTZ-19U-TCS was then double-digested with NcoI and BamHI for 2 hours at 37° C. Thus digested mixture was subjected to low melting agarose gel electrophoresis to obtain a DNA fragment of TCS gene about 750 bp in length. Next, the fragment was ligated overnight using T4 DNA ligase at 4° C. with an expression plasmid vector pET-2d which had been previously double-digested with NcoI and BamHI, thereby obtaining pET-2d-TCS for use in expression.

Example 2

Mutagenesis and Cloning of DNA Encoding MTCS(M177)

Mutagenesis was performed using the Muta-Gene Phagemid in vitro Mutagenesis Kit from Bio-Rad Co. Protocols were followed according to manufacturer's instructions. The pTZ-19U-TCS obtained in example 1 was used as

```
Primer V 5' GTT GTA ACC TCC GGC ATC GCG TTG CTG 3' (SEQ ID NO. 7)
``` the template DNA. Mutagenic primer III was used for site-directed mutagenesis. In short, E. Coli. CJ236 was transformed with pTZ-19U-TCS. The uracil-containing temple DNA was then extracted in the presence of helper phage. Next, the mutagenic strand was synthesized by a series of operations including mixing the uracil-containing template DNA with mutagenic primer, adding T4 DNA ligase, and adding T4 DNA polymerase, etc. Thus mutated DNA was used to transform competent E. Coli. MV1190. Finally, mutant colonies were picked and the mutations were confirmed by sequencing analysis, thereby obtaining pTZ-19U-MTCS(M177).

Mutagenic primer III was designed for this experiment. Primer III 5' AAG CGT GTT GAC GAA ACC TTC CTA CCA 3' (SEQ ID NO.5)

Primer III is characterized in that the codon encoding Lys of position 177 of native TCS is replaced with the codon encoding Glu. Due to codon degeneracy, the underlined codon can also be replaced with other codons encoding Glu, e.g., GAG.

Thus obtained pTZ-19U-MTCS(M177) was then double-digested with NcoI and BamHI to obtain the DNA fragment encoding MTCS(177). Next, the same fragment was ligated with an expression plasmid vector pET-2d which had been previously double-digested with NcoI and BamHI, thereby obtaining pET-2d-MTCS(M177)

Example 3

Mutagenesis and Cloning of DNA Encoding MTCS(203)

For mutagenesis and cloning, the protocols described in example 2 were followed except that a different mutagenic primer IV was designed and used according to the experiment, thereby obtaining pET-2d-MTCS(203).

Mutagenic primer IV was designed for this experiment. Primer IV 5' ATT CAG ATA GCG GGT ACT AAT AAT GGA 3' (SEQ ID NO.6)

Primer IV is designed so that the codon encoding Ser of position 203 of native TCS be replaced with codon encoding Gly. Due to codon degeneracy, the underlined codon can also be replaced with other codons encoding Gly, e.g., GGA, GGC and GGG. That is to say, there are four alternatives for the codon encoding Gly.

Example 4

Mutagenesis and Cloning of DNA Encoding MTCS(236)

For mutagenesis and cloning, the protocols described in example 2 were followed except that a different mutagenic primer V was designed and used according to the experiment, thereby obtaining pET-2d-MTCS(236).

Mutagenic primer V was designed for this experiment.

Primer V is designed so that the codon encoding Asn of position 236 of native TCS be replaced with codon encoding Gly. Due to codon degeneracy, the underlined codon can also be replaced with other codons encoding Gly, e.g., GGA, GGG and GGT.

Example 5

Mutagenesis and Cloning of DNA Encoding MTCS(M177, 203)

For mutagenesis and cloning, the protocols described in example 2 were followed except that two mutagenic primers III and IV were designed and used according to the experiment thereby obtaining pET-2d-MTCS(M177, 203).

```
Primer III  5' AAG CGT GTT GAC GAA ACC TTC CTA CCA 3' (SEQ ID NO. 5)
Primer IV   5' ATT CAG ATA GCG GGT ACT AAT AAT GGA 3' (SEQ ID NO. 6)
```

Primer III is designed so that the codon encoding Lys of position 177 of native TCS be replaced with the codon encoding Glu. Due to codon degeneracy, the underlined codon can also be replaced with other codons encoding Glu, e.g., GAG.

Primer IV is designed so that the codon encoding Ser of position 203 of native TCS be replaced with codon encoding Gly. Due to codon degeneracy, the underlined codon can also be replaced with other codons encoding Gly, e.g., GGA, GGC and GGG.

Example 6

Mtagenesis and Cloning of DNA Encoding MTCS(M177, 203, 236)

For mutagenesis and cloning, the protocols described in example 2 were followed except that three mutagenic primers III, IV and V were designed and used according to the experiment, thereby obtaining pET-2d-MTCS(M177, 203, 236).

```
Primer III  5' AAG CGT GTT GAC GAA ACC TTC CTA CCA 3' (SEQ ID NO. 5)

Primer IV   5' ATT CAG ATA GCG GGT ACT AAT AAT GGA 3' (SEQ ID NO. 6)

Primer V    5' GTT GTA ACC TCC GGC ATC GCG TTG CTG 3' (SEQ ID NO. 7)
```

Primer III is designed so that the codon encoding Lys of position 177 of native TCS be replaced with the codon encoding Glu. Due to codon degeneracy, the underlined codon can also be replaced with other codons encoding Glu, e.g., GAG.

Primer IV is designed so that the codon encoding Ser of position 203 of native TCS be replaced with codon encoding Gly. Due to codon degeneracy, the underlined codon can also be replaced with other codons encoding Gly, e.g., GGA, GGC and GGG.

Primer V is designed so that the codon encoding Asn of position 236 of native TCS be replaced with codon encoding Gly. Due to codon degeneracy, the underlined codon can also be replaced with other codons encoding Gly, e.g., GGA, GGG, and GGT.

Example 7

Expression of TCS

By following standard protocols, calcium chloride-treated competent E. coli BL21 (DE3, plysS) was transformed with plasmid pET-2d-TCS obtained in example 1 containing TCS gene. In short, 1–100 ng of pET-2d-TCS was gently mixed with 100ul of competent cells. After 30 to 60 minutes of holding on ice, the mixture was heat-shocked at 42° C. for 90 seconds and then returned to ice. After 5 minutes the mixture was added 0.5 ml of LB medium and then incubated at 37° C. for 1 hour with aeration. One tenth of thus incubated mixture was diluted with 0.1 ml of LB medium and spread on LB plates containing ampicillin and chloramphenicol. These plates were incubated overnight at 37° C. and then picked for individual colonies with uniform size and shape. The transformant was cultured overnight at 37° C. in LB medium containing ampicillin and chloramphenicol, and then grown in larger scale at the same temperature in M9ZB medium containing ampicillin and chloramphenicol until the cell density reached $A_{57C}$=0.8. IPTG was then added to a final concentration of 0.5 mM and the cells were cultured for another 3 hours. Next, the cells were then collected and lysed by sonication. The lysate was centrifuged and the supernatant was loaded onto a CM-Sephadex or CM-Sepharose column. The column was washed with 50 mM Tris-HCl buffer (pH7.5) containing 0.1 mM phenyl methansulfonyl fluoride (PMSF) until $A_{280}$ dropped to baseline and then it was eluted with linear gradient of 0.1–0.4 M NaCl in the washing butter. The material in the highest peak was the expressed recombinant TCS. The amino acid sequence of the recombinant TCS is shown by amino acid residues 1 through 247 in FIG. 1 with a Met added to its −1 position.

Example 8

Expression of MTCS(M177)

Plasmid pET-2d-MTCS(M177) obtained in example 2 containing DNA encoding MTCS(M177) was used to transform E. coli BL21 (DE3, plysS). Same protocols as described in example 7 were followed for gene transformation, expression and protein purification, thereby obtaining MTCS(M177). The amino acid sequence of MTCS(M177) is identical to that of the recombinant TCS in example 7 except that the Lys of position 177 was replaced with Glu.

Example 9

Expression of MTCS(M203)

Plasmid pET-2d-MTCS(M203) obtained in example 3 containing DNA encoding MTCS(M203) was used to transform E. coli BL21 (DE3, plysS). Same protocols as described in example 7 were followed for gene transformation, expression and protein purification, thereby obtaining MTCS(M203). The amino acid sequence of MTCS(M203) is identical to that of the recombinant TCS in example 7 except that the Ser of position 203 was replaced with Gly.

Example 10

Expression of MTCS(M236)

Plasmid pET-2d-MTCS(M236) obtained in example 4 containing DNA encoding MTCS(M236) was used to transform E. coli BL21 (DE3, plysS). Same protocols as described in example 7 were followed for gene transformation, expression and protein purification, thereby obtaining MTCS (M236). The amino acid sequence of MTCS(M236) is identical to that of the recombinant TCS in example 7 except that the Asn of position 236 was replaced with Gly.

Example 11

Expression of MTCS(M177, 203)

Plasmid pET-2d-MTCS(M177, 203) obtained in example 5 containing MTCS(M177, 203) was used to transform E. coli BL21 (DE3, plysS). Same protocols as described in example 7 were followed for gene transformation, expression and protein purification, thereby obtaining MTCS (M177, 203). The amino acid sequence of MTCS(M177, 203) is identical to that of the recombinant TCS in example 7 except that the Lys of position 177 was replaced with Glu and the Ser of position 203 was replaced with Gly.

Example 12

Expression of MTCS(M177, 203, 236)

Plasmid pET-2d-MTCS(M177, 203, 236) obtained in example 6 containing DNA encoding MTCS(M177, 203, 236) was used to transform E. coli BL21 (DE3, plysS). Same protocols as described in example 7 were followed for gene transformation, expression and protein purification, thereby obtaining MTCS(M177, 203, 236). The amino acid sequence of MTCS(M177, 203, 236) is identical to that of the recombinant TCS in example 7 except that the Lys of position 177 was replaced with Glu, the Ser of position 203 was replaced with Gly, and the Asn of position 236 was replaced with Gly.

Example 13

Assays for the Biological Activities and the Immunological Reactivities of MTCS(M177)

RIP activity was determined as described by Pelhem & Jackson (H. K. B. Pelhem and R. J. Jackson, Eur. J. Biochem. 67: 247–256, 1976). Rabbit reticulocyte lysate was obtained from Promega. [$^3$H]-leucine was obtained from New England Nuclear. Abortifacient activity assay was conducted following standard protocols of the present inventors' laboratory (Nie H L, et al., Position 120–123, a Potential Active Site of Trichosanthin, Life Sciences, 62 (6): 491–500, 1998), using eleven-day pregnant ICR mice. Animals were sacrificed and dissected 48 hours after dorsal injection of 75 nmol/Kg of MTCS(M177). The numbers of total and dead fetuses (including absorbed embryos) were recorded, and the fetus death ratio was calculated. In vitro immunological reactivity was measured by competitive ELISA. IgG antibody and monoclonal IgE antibody were prepared and purified by the present inventors' laboratory (He X H, et al., Acta Biochemia et Biophysica Sinica, 26: 657–662, 1994). Antibody was purified by immunoaffinity chromatography. Native TCS was used as the positive control in all the assays described in this example. The results are listed in Table 7.

TABLE 7

Assays for the biological activities and the immunological reactivities of MTCS(M177)

| Product | Position of Modified Amino Acid | RIP Activity (%) | Abortifacient Activity (%) | In vitro Reactivity with IgG | In vitro Reactivity with IgE |
|---|---|---|---|---|---|
| Native TCS | 0 | ++* | ++ | ++ | ++ |
| MTCS(M177) | 177 | ++ | ++ | ± | ± |

*Please refer to Table 4 for details of values represented by symbols "+", "−" and the like in examples 13 to 17.

Example 14

Assays for the Biological Activities and the Immunological Reactivities of MTCS(M203)

Same methods as described in example 13 were used to determine RIP activity, abortifacient activity and in vitro immunological reactivity of MTCS(M203). Native TCS was used as the positive control in all of these assays. The results are listed in Table 8.

TABLE 8

Assays for the biological activities and the immunological reactivities of MTCS(M203)

| Product | Position of Modified Amino Acid | RIP Activity (%) | Abortifacient Activity (%) | In vitro Reactivity with IgG | In vitro Reactivity with IgE |
|---|---|---|---|---|---|
| Native TCS | 0 | ++ | ++ | ++ | ++ |
| MTCS(M203) | 203 | ++ | ++ | ± | ± |

Example 15

Assays for the Biological Activities and the Immunological Reactivities of MTCS(M236)

Same methods as described in example 13 were used to determine RIP activity, abortifacient activity and in vitro immunological reactivity of MTCS(M236). Native TCS was used as the positive control in all of these assays. The results are listed in Table 9.

TABLE 9

Assays for the biological activities and the immunological reactivities of MTCS(M236)

| Product | Position of Modified Amino Acid | RIP Activity (%) | Abortifacient Activity (%) | In vitro Reactivity with IgG | In vitro Reactivity with IgE |
|---|---|---|---|---|---|
| Native TCS | 0 | ++ | ++ | ++ | ++ |
| MTCS(M236) | 236 | ++ | ++ | + | + |

Example 16

Assays for the Biological Activities and the Immunological Reactivities of MTCS(M177, 203)

Same methods as described in example 13 were used to determine RIP activity, abortifacient activity and in vitro immunological reactivity of MTCS(M177, 203). Native TCS was used as the positive control in all of these assays. The results are listed in Table 10.

TABLE 10

Assays for the biological activities and the immunological reactivities of MTCS(M177, 203)

| Product | Position of Modified Amino Acid | RIP Activity (%) | Abortifacient Activity (%) | In vitro Reactivity with IgG | In vitro Reactivity with IgE |
|---|---|---|---|---|---|
| Native TCS | 0 | ++ | ++ | ++ | ++ |
| MTCS(M177, 203) | 177, 203 | ++ | ++ | −(a) | −(a) |

Example 17

Assays for the Biological Activities and the Immunological Reactivities of MTCS(M177, 203, 236)

Same methods as described in example 13 were used to determine RIP activity, abortifacient activity and in vitro immunological reactivity of MTCS(M177, 203, 236). Native TCS was used as the positive control in all of these assays. The results are listed in Table 11.

TABLE 11

Assays for the biological activities and the immunological reactivities of MTCS(M177, 203, 236)

| Product | Position of Modified Amino Acid | RIP Activity (%) | Aborti-facient Activity (%) | In vitro Reactivity with IgG | In vitro Reactivity with IgE |
|---|---|---|---|---|---|
| Native TCS | 0 | ++ | ++ | ++ | ++ |
| MTCS(M177, 203, 236) | 177, 203, 236 | ++ | ++ | –(b) | –(b) |

Example 18

Toxicity of MTCS (M177) Against K562 Cells

The toxicity of MTCS(M177) against human chronic myelogenous leukemia K562 cells and normal human lymphocytes was tested by performing a MTT (3-(4,5-dimethylthiazol-2-yl)-2,5-diphenyl tetrazolium bromide) cytotoxicity assay. For each type of cells, approximately 200,000 cells grown in RPMI 1640 medium supplemented with 10% fetal bovine serum were seeded into each well of the culture plate at 37° C., 5% $CO_2$ and incubated with MTCS(M177). The concentrations of MTCS(M177) are 1, 5, 10, 20, 50, and 100 ug/ml respectively. The assay was terminated after 48 hours by adding 25 ul MTT (Sigma, 5 mg/ml) to each well, then incubating for two additional hours, and finally adding lysing buffer to each well to lyse the cells. After incubating overnight at 37° C., the plate was read spectrophotometrically at 570 nm. The $LC_{50}$ of MTCS(M177) for K562 cells was calculated to be less than 30 ug/ml. Normal human lymphocytes were not sensitive to MTCS(M177) because no $LC_{50}$ value could be obtained at a MTCS(M177) concentration as high as 1000 ug/ml.

Example 19

Toxicity of MTCS (M203) Against K562 Cells

Same methods as described in example 18 were used to determine the toxicity of MTCS(M203) against human chronic myelogenous leukemia K562 cells and normal human lymphocytes. The $LC_{50}$ of MTCS(M203) for K562 cells was calculated to be less than 30 ug/ml. Normal human lymphocytes were not sensitive to MTCS(M203) because no $LC_{50}$ value could be obtained at a MTCS(M203) concentration as high as 1000 ug/ml.

Example 20

Toxicity of MTCS (M236) Against K562 Cells

Same methods as described in example 18 were used to determine the toxicity of MTCS(M236) against human chronic myelogenous leukemia K562 Cells and normal human lymphocytes. The $LC_{50}$ of MTCS(M236) for K562 cells was calculated to be less than 30 ug/ml. Normal human lymphocytes were not sensitive to MTCS(M236) because no $LC_{50}$ value could be obtained at a MTCS(M236) concentration as high as 1000 ug/ml.

Example 21

Toxicity of MTCS (M177, 203) Against K562 Cells

Same methods as described in example 18 were used to determine the toxicity of MTCS(M177, 203) against human chronic myelogenous leukemia K562 cells and normal human lymphocytes. The $LC_{50}$ of MTCS(M177, 203) for K562 cells was calculated to be less than 30 ug/ml. Normal human lymphocytes were not sensitive to MTCS(M177, 203) because no $LC_{50}$ value could be obtained at a MTCS (M177, 203) concentration as high as 1000 ug/ml.

Example 22

Toxicity of MTCS (M177, 203, 236) Against K562 Cells

Same methods as described in example 18 were used to determine the toxicity of MTCS(M177, 203, 236) against human chronic myelogenous leukemia K562 cells and normal human lymphocytes. The $LC_{50}$ of MTCS(M177, 203, 236) for K562 cells was calculated to be less than 30 ug/ml. Normal human lymphocytes were not sensitive to MTCS (M177, 203, 236) because no $LC_{50}$ value could be obtained at a MTCS(M177, 203, 236) concentration as high as 1000 ug/ml.

What is claimed is:

1. A mutant trichosanthin (MTCS) protein, comprising the amino acid sequence as set forth in SEQ ID NO:8, comprising a modification of at least one amino acid residue in the region of amino acid residues 174 to 180, wherein said at least one amino acid residue modification is selected from the group consisting of:
arginine at position 174 and lysine at position 177 are independently replaced with glutamic acid, aspartic acid, or glycine;
aspartic acid at position 176 is independently replaced with lysine or glycine;
threonine at position 178 is independently replaced with glycine or alanine; and
valine at position 175, phenylalanine at position 179, and leucine at position 180 are independently deleted.

2. A mutant protein according to claim 1, further comprising the additional modification of at least one amino acid residue in the region of amino acid residues 203 to 226.

3. A mutant protein according to claim 2, wherein lysine at position 177 is replaced with glutamic acid, and seine at position 203 is replaced with glycine.

4. A mutant protein according to claim 2, wherein lysine at position 177 is replaced with glutamic acid, serine at position 203 is replaced with glycine, and asparagine at position 236 is replaced with glycine.

5. A mutant protein according to claim 2, wherein the amino acid residue arginine at positions 222 is independently replaced with glutamic acid, aspartic acid, or glycine.

6. A mutant protein according to claim 2, wherein at least one amino acid residue selected from the group consisting of asparagine at position 205, asparagine at position 206, glutamine at position 208, glutamic acid at position 210, asparagine at position 217, glutamine at position 219, asparagines at position 220, glutamine at position 221 is independently replaced with lysine or glycine.

7. A mutant protein according to claim 2, wherein at least one amino acid residue selected from the group consisting of serine at position 203, threonine at position 204, serine at position 211, threonine at position 224, threonine at position 226 is independently replaced with glycine or alanine.

8. A mutant protein according to claim 2, wherein at least one amino acid residue is selected from the group consisting of glycine at position 207, phenylalanine at position 209, proline at position 212, valine at position 213, valine at position 214, valine at position 215, valine at position 223, isoleucine at position 216, isoleucine at position 225, alanine at position 218 is independently deleted.

9. A mutant protein according to claim 2, further comprising the additional modification of at least one amino acid residue in the region of amino acid residues 230 to 244.

10. A mutant protein according to claim 9, wherein the amino acid residue arginine at position 243 is independently replaced with glutamic acid, aspartic acid, or glycine.

11. A mutant protein according to claim 9, wherein at least one amino acid residue selected from the group consisting of asparagine at position 236, asparagine at position 242, and asparagine at position 244 is independently replaced with lysine or glycine.

12. A mutant protein according to claim 9, wherein at least one amino acid residue selected from the group consisting of threonine at position 234, and serine at position 235 is independently replaced with glycine or alanine.

13. A mutant protein according to claim , wherein at least one amino acid residue is selected from the group consisting of alanine at position 230, alanine at position 238, glycine at position 231, valine at position 232, valine at position 233, isoleucine at position 237, leucine at position 239, leucine at position 240, and leucine at position 241 is independently deleted.

14. A pharmaceutical composition comprising a mutant protein as defined in claims 1, 2 or 9 and a pharmaceutically acceptable carrier or excipient.

* * * * *

```
                        SEQUENCE LISTING

<160> NUMBER OF SEQ ID NOS: 7

<210> SEQ ID NO 1
<211> LENGTH: 289
<212> TYPE: PRT
<213> ORGANISM: Trichosanthes Kirilowii M.

<400> SEQUENCE: 1

Met Ile Arg Phe Leu Val Leu Ser Leu Leu Ile Leu Thr Leu Phe Leu
1               5                   10                  15

Thr Thr Pro Ala Val Glu Gly Asp Val Ser Phe Arg Leu Ser Gly Ala
            20                  25                  30

Thr Ser Ser Ser Tyr Gly Val Phe Ile Ser Asn Leu Arg Lys Ala Leu
        35                  40                  45

Pro Asn Glu Arg Lys Leu Tyr Asp Ile Pro Leu Leu Arg Ser Ser Leu
    50                  55                  60
```

```
Pro Gly Ser Gln Arg Tyr Ala Leu Ile His Leu Thr Asn Tyr Ala Asp
 65                  70                  75                  80

Glu Thr Ile Ser Val Ala Ile Asp Val Thr Asn Val Tyr Ile Met Gly
                 85                  90                  95

Tyr Arg Ala Gly Asp Thr Ser Tyr Phe Phe Asn Gly Ala Ser Ala Thr
            100                 105                 110

Glu Ala Ala Lys Tyr Val Phe Lys Asp Ala Met Arg Lys Val Thr Leu
        115                 120                 125

Pro Tyr Ser Gly Asn Tyr Glu Arg Leu Gln Thr Ala Ala Gly Lys Ile
    130                 135                 140

Arg Glu Asn Ile Pro Leu Gly Leu Pro Ala Leu Asp Ser Ala Ile Thr
145                 150                 155                 160

Thr Leu Phe Tyr Tyr Asn Ala Asn Ser Ala Ala Ser Ala Leu Met Val
                165                 170                 175

Leu Ile Gln Ser Thr Ser Glu Ala Ala Arg Tyr Lys Phe Ile Glu Gln
            180                 185                 190

Gln Ile Gly Lys Arg Val Asp Lys Thr Phe Leu Pro Ser Leu Ala Ile
        195                 200                 205

Ile Ser Leu Glu Asn Ser Trp Ser Ala Leu Ser Lys Gln Ile Gln Ile
    210                 215                 220

Ala Ser Thr Asn Asn Gly Gln Phe Glu Ser Pro Val Val Leu Ile Asn
225                 230                 235                 240

Ala Gln Asn Gln Arg Val Thr Ile Thr Asn Val Asp Ala Gly Val Val
                245                 250                 255

Thr Ser Asn Ile Ala Leu Leu Leu Asn Arg Asn Asn Met Ala Ala Met
            260                 265                 270

Asp Asp Asp Val Pro Met Thr Gln Ser Phe Gly Cys Gly Ser Tyr Ala
        275                 280                 285

Leu
```

<210> SEQ ID NO 2
<211> LENGTH: 870
<212> TYPE: DNA
<213> ORGANISM: Trichosanthes Kirilowii M.

<400> SEQUENCE: 2

```
atgatcagat tcttagacct ctctttgcta attctcaccc tcttcctaac aactcctgct    60
gtggagggcg atgttagctt ccgtttatca ggtgcaacaa gcagttccta tggagttttc   120
atttcaaatc tgagaaaagc tcttccaaat gaaaggaaac tgtacgatat ccctctgtta   180
cgttccagtc ttccaggttc tcaacgctac gcattgatcc atctcacaaa ttacgccgat   240
gaaaccattt cagtggccat agacgtaacg aacgtctata ttatgggata tcgcgctggc   300
gatacatcct attttttcaa cgaggcttct gcaacagaag ctgcaaaata tgtattcaaa   360
gacgctatgc gaaagttac gcttccatat tctggcaatt acgaaaggct tcaaactgct   420
gcaggcaaaa taagggaaaa tattccgctt ggactccctg cttttggacag tgccattacc   480 actttgtttt actacaacgc caattctgct gcgtcggcac ttattgtact cattcagtcg   540
acgtctgagg ctgcgaggta taaatttatt gagcaacaaa ttgggaagcg tgttgacaaa   600
accttcctac caagtttagc aattataagt ttggaaaata gttggtctgc tctctccaag   660
caaattcaga tagcgagtac taataatgga cagtttgaaa gtcctgttgt gcttataaat   720
gctcaaaacc aacgagtcac gataaccaat gttgatgctg gagttgtaac ctccaacatc   780
```

-continued

```
gcgttgctgc tgaatagaaa caatatggca gccatggatg acgatgttcc tatgacacag        840
agctttggat gtggaagtta tgctatttag                                         870
```

<210> SEQ ID NO 3
<211> LENGTH: 21
<212> TYPE: DNA
<213> ORGANISM: artificial sequence
<220> FEATURE:
<223> OTHER INFORMATION: primer

<400> SEQUENCE: 3

```
gtgcaggcca tggatgttag g                                                  21
```

<210> SEQ ID NO 4
<211> LENGTH: 30
<212> TYPE: DNA
<213> ORGANISM: artificial sequence
<220> FEATURE:
<223> OTHER INFORMATION: primer

<400> SEQUENCE: 4

```
aacaatatgg cataggatcc catggatgac                                         30
```

<210> SEQ ID NO 5
<211> LENGTH: 27
<212> TYPE: DNA
<213> ORGANISM: artificial sequence
<220> FEATURE:
<223> OTHER INFORMATION: primer

<400> SEQUENCE: 5

```
aagcgtgttg acgaaacctt cctacca                                            27
```

<210> SEQ ID NO 6
<211> LENGTH: 27
<212> TYPE: DNA
<213> ORGANISM: artificial sequence
<220> FEATURE:
<223> OTHER INFORMATION: primer

<400> SEQUENCE: 6

```
attcagatag cgggtactaa taatgga                                            27
```

<210> SEQ ID NO 7
<211> LENGTH: 27
<212> TYPE: DNA
<213> ORGANISM: artificial sequence
<220> FEATURE:
<223> OTHER INFORMATION: primer

<400> SEQUENCE: 7

```
gttgtaacct ccggcatcgc gttgctg                                            27
```